United States Patent [19]

Nesbitt

[11] Patent Number: 4,718,412
[45] Date of Patent: Jan. 12, 1988

[54] DISPOSABLE CERVICAL IMMOBILIZATION MEANS

[76] Inventor: William R. Nesbitt, 9697 Blue Oak La., Loomis, Calif. 95650

[21] Appl. No.: 871,390

[22] Filed: Jun. 6, 1986

Related U.S. Application Data

[63] Continuation-in-part of Ser. No. 650,206, Sep. 13, 1984, Pat. No. 4,594,999.

[51] Int. Cl.[4] .............................................. A61F 5/04
[52] U.S. Cl. ................................... 128/87 R; 128/134; 128/78
[58] Field of Search ..................... 128/87 R, 87 B, 88, 128/78, 133, 134, 85

[56] References Cited

U.S. PATENT DOCUMENTS

| | | | |
|---|---|---|---|
| 2,409,195 | 10/1946 | Crawford | 128/87 R |
| 3,732,863 | 5/1973 | Harrington | 128/84 C |
| 3,850,167 | 11/1974 | Seeley | 128/87 R |
| 4,143,654 | 3/1979 | Sherman | 128/87 R |
| 4,211,218 | 7/1980 | Kendrick | 128/134 X |
| 4,589,407 | 5/1986 | Koledin et al. | 128/87 R |

*Primary Examiner*—Robert A. Hafer
*Assistant Examiner*—Samuel Rimell
*Attorney, Agent, or Firm*—Mark C. Jacobs

[57] ABSTRACT

A disposable lightweight, readily stored, low cost cervical spine board made of wax coated or plastic coated reinforced double walled corrugated board. The device has pre-cut score lines therein for folding the device around the sides of the head and around the sides of the body.

Head and neck tabs, and body wings are secured by duct tape or other suitable two inch tape, which tape may optionally be preattached to the device.

19 Claims, 7 Drawing Figures

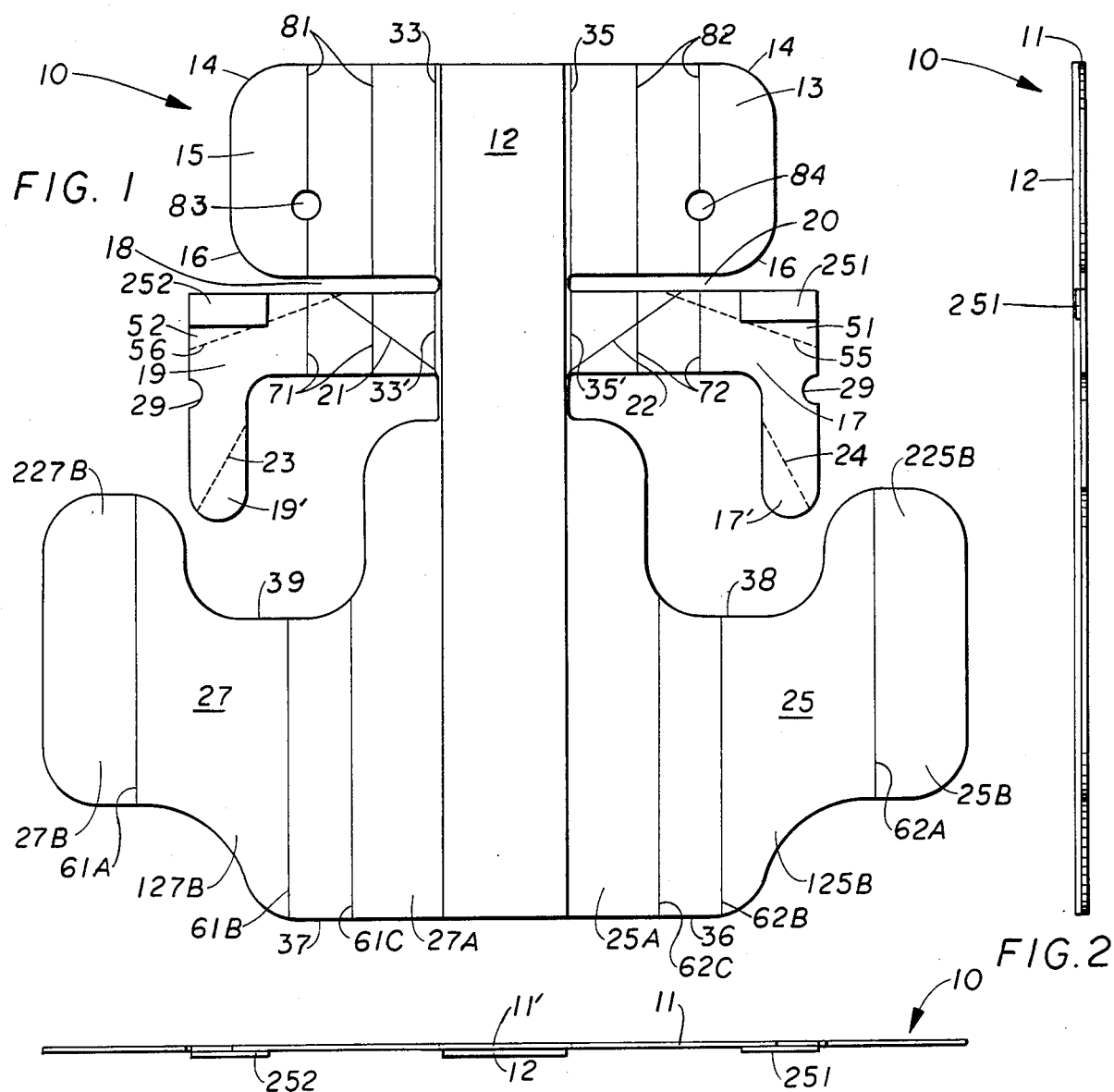
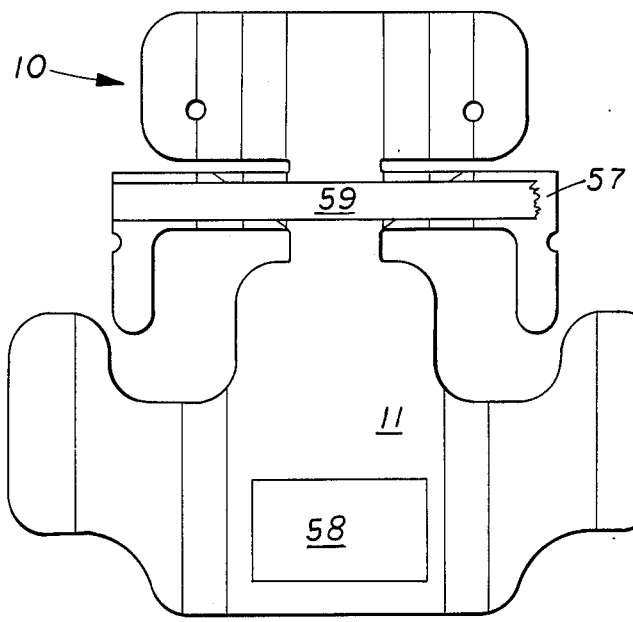

DISPOSABLE CERVICAL IMMOBILIZATION MEANS

RELATION TO OTHER APPLICATIONS

This application is a continuation in part of my copending application Ser. No. 650,206 filed Sept. 13, 1984, and now U.S. Pat. No. 4,594,999 issued June 17, 1986.

BACKGROUND OF THE INVENTION

1. Field of the Invention

This invention relates in general to devices for immobilizing the human head, neck and torso and relates more particularly to such devices for use in emergency situations to immobilize the body to prevent further injury to the potentially injured cervical spine.

2. Description of the Prior Art

Numerous devices have been proposed in the past to perform the function of immobilizing or stabilizing the human head and neck for emergency purposes. Such devices are extremely important, particularly in emergency situations, in the handling of possible fractures of the cervical spine. In the cases of industrial injuries, automobile accidents and battlefield injuries. It is usually necessary to remove the patient from the injury scene, often under conditions of stress or time pressure, for transportation to medical facilities. This removal is almost always accomplished by personnel who are not medical doctors, although they may have had varying amounts of education and training in the handling of injured patients.

In the handling and moving, there is a high risk of aggravation of injuries to the cervical spine if the patient's head and neck are not properly immobilized or stabilized.

Many prior art U.S. patents disclose devices comprising a rigid board member having straps attached thereto for attachment to a patient to immobilize the head and neck. These devices provide a rigid structure for completely preventing lateral motion and rotation of the patient's head but are expensive, bulky and complicated to use. Because of their cost, emergency personnel can usually afford to have only one device with them. This not only makes proper immobilization impossible of other injured patients in the same accident but also prevents the emergency personnel from returning to duty until their board is returned. Further the board may not be removed until x-rays have ruled out neck or back injuries. The wood or metal devices presently used allows only very poor quality films when x-rays are shot through them.

There is a need, therefore, for a disposable, inexpensive readily stackable, more radiolucent C-spine immobilizer that can be employed easily by non-physician personnel.

It is another object to provide a cervical spine immobilizer that is easily and quickly applied to injured persons.

Still another object is to provide a spine board that can be stored in large quantities in very little space.

Yet another object is to provide a light weight spine board that is suitable for disaster situations which can be purchased in large quantities at modest expense.

These and other objects of the invention will in part be obvious and will in part appear hereinafter.

The invention accordingly comprises the product possessing the features, properties and the relation of elements which are exemplified in the following detailed disclosure and the scope of the application of which will be indicated in the claims.

For a fuller understanding of the nature and objects of the invention, reference should be had to the following detailed description taken in connection with the accompanying drawings.

DESCRIPTION OF THE FIGURES

FIG. 1 is a front elevational view of the device of this invention.

FIG. 2 is a side elevation view thereof.

FIG. 3 is a top plan view.

FIG. 4 is a rear elevational view of the device of this invention.

SUMMARY OF THE INVENTION

A cervical spline immobilization device is provided that comprises a double walled corrugated board member, or a member of similar material. The device includes a reinforcement panel at a critical central zone. Various portions of the device are held together by standard duct tape or other two inch readily available adhesive tape. Alternatively the tape can be pre-attached in part and left dangling in part, the unattached part having a protective removable backing.

The device is adapted for easy storage and use in emergency medical treatment situations.

DESCRIPTION OF THE PREFERRED EMBODIMENT

Figure 6:
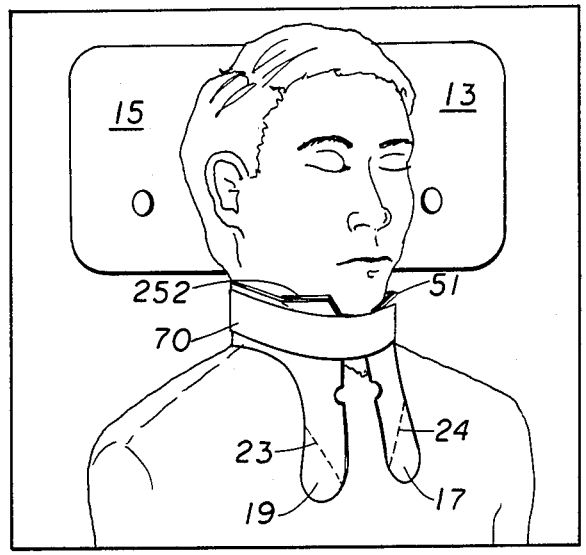

The device of this invention is formed perferably of a double walled, corrugated cardboard which has been retreated on both the front and rear surfaces with a coating of wax or other suitable water resistant material. The device as seen in FIG. 1 has a reinforcing member that is vertically disposed down the front surface of the device. The front surface is defined as the surface in contact with the body or clothing of the user. Reference is made to FIG. 1 which depicts the device and to FIG. 6 showing it disposed in place on an ambulatory patient.

As seen in FIG. 2 device 10 has a main body portion 11 which includes a generally longitudinal elongated center reinforcement portion 12 which comprises preferably three (3) thicknesses of corrugated board or some other inexpensive, rigid material such as ¼" plywood, mounted thereon as by stapling or adhesing to the central section 11' of main body 11. Depending outwardly at the top of main body 11 are head flanges 13 and 15. These are generally rectangular of double thickness with preferably round upper corners 14 and lower corners 16. See FIG. 1.

Disposed just below said head flanges and also extending outwardly on either side of said center portion 12 are the neck collar members 17 and 19. Fold lines 33 and 35 form the interior edge of both head flanges while the hard neck collar members 17 and 19 have fold lines designated 33' and 35'.

Intermediate vertical fold lines 81 and 82 are spaced substantially equidistant from the outer vertical edge of each head flange and the respective interior fold lines 33 and 35. Optionally a throughbore 83, 84 may be made in the head flange of about 1" diameter, spaced up about 4" on the first inwardly intermediate fold line 81 and 82. These throughbores serve as a guide means for sound directed to the ears of the patient such that when the head flange is positioned as shown in FIG. 7, the patient can still hear.

Slots 18 and 20, usually about ½" in elevation, are cut through to isolate the bottom edge of each head flange from its adjacent collar member.

The hard collar members 17 and 19 comprise generally outwardly extending, mirror image, 90° inwardly inverted, boot-like portions secured to or integrally formed with central member 11'. These include vertical fold lines 71 and 72. Portions 17 and 19 each include a built in triangular chin tab 51 and 52 within the upper distal corner relative to the central reinforcement portion 12. These chin tabs are preferably padded on the front surface, e.g. with a urethane foam layer 251 and 252, which is visible in FIG. 1. Diagonal score lines 55 and 56 are used to fold back these built in chin tabs 51 and 52 to conform to the bone structure of the patient. Note the angularity as in FIG. 5 of the chin tab. The boot-like portions 17 and 19 also have rounded edges at the lower end thereof, again to avoid injury to the patient.

Figure 5:
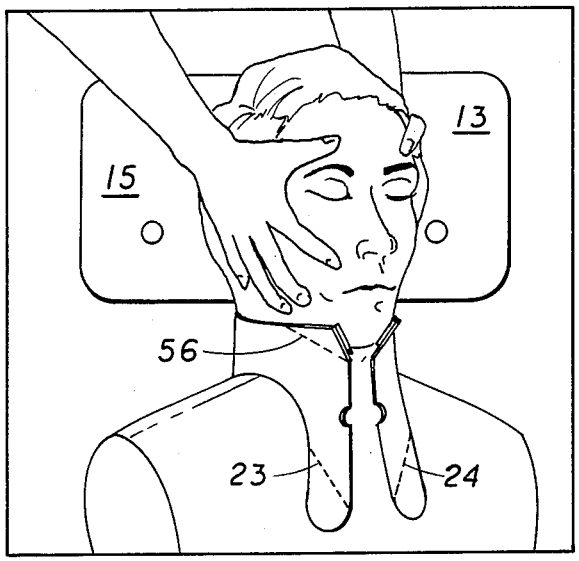
FIGS. 5, 6 and 7, are perspective views illustrating the use of the instant device to immobilize a human being.
Figure 7:
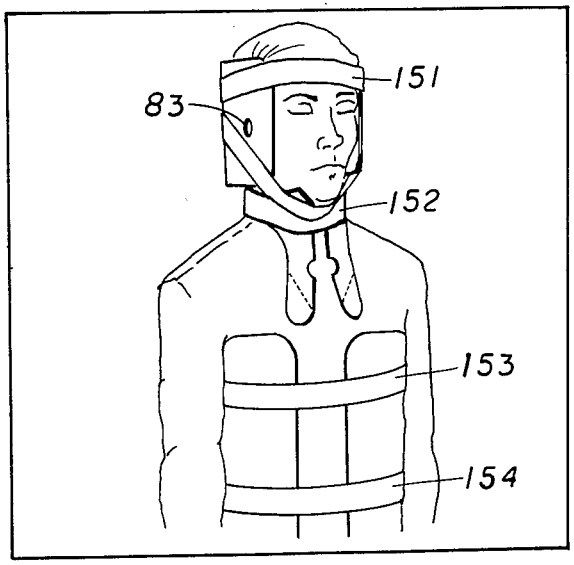

Upper score lines 21 and 22 and lower score lines 23 and 24, are used in the positioning of the collar members 17 and 19 relative to the patient as seen in FIGS. 5-7. The upper score lines 21 and 22 are used, especially in close quarters, to lift the collar members 17, 19 over the shoulders of the supine patient without tearing the collar members. After the descending segments 17' and 19' are over the shoulders, the upper score lines are no longer employed.

The lower score lines 23, 24 are bent outward to allow a flat surface to press against the patient's chest in order to complete the support of the collar members 17, 19.

Score lines are to be differentiated from fold lines in that score lines are diagonal, while fold lines are vertical as used here.

An optional, but preferred hemisperical cutout 29 may be made on the edge of the members 17 and 19 to permit an easy wide access to the throat should a tracheotomy be necessary.

In this invention the dispostion of the collar is key, since it serves to center the board 10 on the patient in contrast to virtually every other vest type spinal immobilization device wherein the patient is centered by the body flanges.

The single thickness body members 25 and 27 are each disposed on opposite sides of the central section 11' and are preferably integrally formed therewith since they too are of double walled corrugated board or other similar material to the head flanges and collar members.

Body members 25 and 27 each include several segments. The first of these are L-shaped, outwardly extending mirror image segments 25A and 27A which are disposed adjacent to the central section 11' as reinforced by elongated member 12. Each of these segments extends outwardly to a vertical fold line 61B and 62B respectively.

The intermediate fold lines 61C and 62C respectively are vertically aligned with the interior intermediate fold lines 81 and 82 on head flanges 15 and 13 respectively.

The wing segments 25B and 27B commence along the fold lines 61B and 62B and comprise two parts. The first part consists of quadralaterals, 125B and 127B and which each extend generally outwardly and then upwardly convex arcuately from the fold lines 61C, 62C; and outwardly and then concave arcuately upwardly from the fold lines 61B and 62B, to their terminal ends at the intersections of the second part of the wing segments, 225B and 227B. These wing segments are the second parts 225B and 227B and are each generally rectangular with each of the two corners being preferably rounded for the comfort of the patient. Vertical fold line 61A and 62A are spaced inwardly from the outer edge of the second segments.

DISPOSITION UPON AN INJURED PARTY

While the device can be positioned on a patient by a single rescuer, the use of two persons who are adequately trained in C-spine immobilization techniques is recommended.

First, position the collar. This is achieved by bending the chin tabs 51 and 52 back at the pre-scored cuts 56 and 55 per FIG. 1 and FIG. 4. After the collar is positioned to hold the head in place, if necessary fold the creases 21, 22 outwardly to clear the shoulders. Reference is made to FIG. 4. The small rubber pads seen in FIGS. 1 and 5, 252 and 251 are to be placed just under the outer edges of the jaw per FIG. 5. If necessary bend the lower portion of the collar outward as needed to keep the neck of the patient in a neutral position.

Next, the two inch tape 70, is to be applied at the locations designated 151, 152, 153 and 154 as per FIGS. 5 and 6. Those locations are, as seen in the 6th Figure, at (1) across the torso flanges (2) across the collar; (3) beneath the head under the collar flanges; and across the forehead. As a caution, the rescuers are advised to make sure that there is no pressure being applied against the trachea or the carotid arteries or throat. Duct tape may be used, but is not recommended as it has poor adhesive qualities under extreme temperature conditions. Surgical tape or other cloth back adhesive tape is therefore recommended.

The instant device is intended for a one time usage, after which it is to be discarded. In view of its throwaway nature, it is not intended to be used for the vertical lifting of a sitting patient, nor for the dragging of an injured party from the scene of an incident as by pulling on the device.

The corrugated double walled board recommended for this device should be dipped sprayed or otherwise coated with a waterproofing agent such as a wax or plastic coating on both the front and rear surface of the device.

Optionally as seen in the rear view FIG. 4, a clear plastic tape reinforcing layer 59, may be placed transversely across the full width of the collar members at location 57. Printed indicia such as instructions, product safety information and the like can be printed at various locations such as 58. before the waterproofing treatment.

The device of this invention is seen to provide the dual benefit of both C-spine immobilization, as well as providing a built in hard cervical collar to rigidify the head of an injured patient.

Since certain changes may be made in the above article without departing from the scope of the invention herein involved. It is intended that all matter contained in the above description and shown in the accompanying drawings shall be interpreted as illustrative and not in a limiting sense.

What is claimed is:

1. A cervical spine board adapted to restrain the head and body of an injured person comprising
a main body portion, and
a flat, elongated, central reinforcement portion of a rectangular configuration, of similar length to that of the main body, portion,
said main body portion having a central section,
a pair of head flanges, one of which extends outwardly on either side of said central section and which flanges are capable of moving from a first position in the same plane as said central member to a second position generally normally upward from said central section,
a hard neck collar comprising
a pair of neck collar members, one on each side of the central portion, extending outwardly from said central section and extending further than said head flanges, movable from a first position in the same plane as said head flanges, to a position substantially parallel to each other, along the sides of the neck,
each neck collar member being a downward L shaped unit, and having built in outwardly foldable chin tab,
said chin tab formed by a score line located at the intersection of two legs,
a pair of body members, one on each side of said central portion, said body members including a first L-shaped segment adjacent to said central member and a wing segment capable of moving from a first position in the same plane as the central portion upwardly and inwardly toward the other of said wing segments to a spaced relationship second position spaced from the other of said wing members.

2. In the device of claim 1 wherein a fold line separates each L-shaped body member segment from its respective wing member.

3. In the device of claim 1 wherein each wing member has a right angle notched corner.

4. In the device of claim 1 wherein the collar members have a descending section with a hemisperical cut out on the exterior edge thereof.

5. In the device of claim 1 wherein a fold line separates the head flanges and the collar member from the central section.

6. In the device of claim 1 wherein the device is constituted of double walled, corrugated board, main body portion, and a unitary reinforcement center portion, that is attached to said main body portion.

7. In the device of claim 1 wherein each head flange includes a throughbore to serve as a sound director.

8. In the device of claim 1 wherein the chin tabs also include a padding on the front surface thereof.

9. In the device of claim 1 wherein each body member has a U-shaped top edge spaced down from its respective collar member.

10. In the device of claim 9 wherein the body members have a notched lower, outer corner.

11. In the device of claim 1 wherein the head flanges are rounded at their corners and include a plurality of horizontally spaced vertical fold lines.

12. In the device of claim 1 wherein the collar members extend outward from said central section more than said head flanges but less than said body members.

13. In the device of claim 11 wherein the collar members extend outward from said central section more than said head flanges but less than said body members.

14. In the device of claim 11 wherein the collar members also include a plurality of horizontally spaced vertical fold lines.

15. In the device of claim 14 wherein the collar members each include an exterior edge hemispherical cut out, and a foldable padded built in chin tab.

16. In the device of claim 15 wherein the body members have a plurality of horizontally spaced vertical fold lines 17. In the device of claim 16 wherein the central portion is composed of plywood.

18. In the device of claim 14 wherein the collar members have a front and rear side surface, and a top edge thereof, the rear surface being reinforced, each member also having a trio of angular score lines thereon, two of which commence from said top edge.

19. In the device of claim 4 wherein the collar members each have a foldable built in chin tab which have a urethane pad on the front side thereof, and said collar members also have a diagonal score line to ease the fitting of same over the shoulder of a patient, and a second diagonal score line lower than said first mentioned score line for patient comfort.

* * * * *